United States Patent
Crawford et al.

(10) Patent No.: US 11,523,785 B2
(45) Date of Patent: Dec. 13, 2022

(54) INCREASED CONE BEAM COMPUTED TOMOGRAPHY VOLUME LENGTH WITHOUT REQUIRING STITCHING OR LONGITUDINAL C-ARM MOVEMENT

(71) Applicant: GLOBUS MEDICAL, INC., Audubon, PA (US)

(72) Inventors: Neil R. Crawford, Chandler, AZ (US); Norbert Johnson, North Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 111 days.

(21) Appl. No.: 17/030,581

(22) Filed: Sep. 24, 2020

(65) Prior Publication Data
US 2022/0087628 A1 Mar. 24, 2022

(51) Int. Cl.
*A61B 6/00* (2006.01)
*A61B 6/03* (2006.01)

(52) U.S. Cl.
CPC ............ *A61B 6/4441* (2013.01); *A61B 6/032* (2013.01); *A61B 6/466* (2013.01); *A61B 6/54* (2013.01)

(58) Field of Classification Search
CPC ..... A61B 6/4441; A61B 6/4405; A61B 6/547; A61B 6/032; A61B 6/035; A61B 6/4085; A61B 6/56; A61B 6/463; A61B 6/025; A61B 6/03; A61B 6/466; A61B 6/4021; A61B 6/4435; A61B 6/4464; A61B 2090/3762; A61B 6/4476; G06T 2207/10081; G06T 2211/40
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |

(Continued)

OTHER PUBLICATIONS

US 8,231,638 B2, 07/2012, Swarup et al. (withdrawn)

*Primary Examiner* — Don K Wong

(57) ABSTRACT

A medical imaging system includes a movable station having a C-arm, a collector, an X-ray beam emitter, and a controller. The collector is attached to a first end of the C-arm. The X-ray beam emitter faces the collector to emit an X-ray beam in a direction of the collector and is attached to a second end of the C-arm. The controller moves one of the X-ray beam emitter and the collector to a first offset position along a lateral axis orthogonal to the arc, and obtains a first set of images by rotating the collector and the X-ray beam emitter along the arc about a scanned volume. The controller moves the one of the X-ray beam emitter and the collector to a second offset position along the lateral axis, and obtains a second set of images. The controller combines the first and second set of images to generate a three-dimensional image of the scanned volume.

11 Claims, 20 Drawing Sheets

(56) References Cited

U.S. PATENT DOCUMENTS

| | | |
|---|---|---|
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Winash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |

(56) References Cited

U.S. PATENT DOCUMENTS

| | | |
|---|---|---|
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 3,035,685 A1 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |

(56) References Cited

U.S. PATENT DOCUMENTS

| | | |
|---|---|---|
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Greer et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |

(56) References Cited

U.S. PATENT DOCUMENTS

| | | |
|---|---|---|
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0176717 A1* | 7/2011 | Siren ............ A61B 6/4435 382/131 |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |

(56) References Cited

U.S. PATENT DOCUMENTS

| | | |
|---|---|---|
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

\* cited by examiner

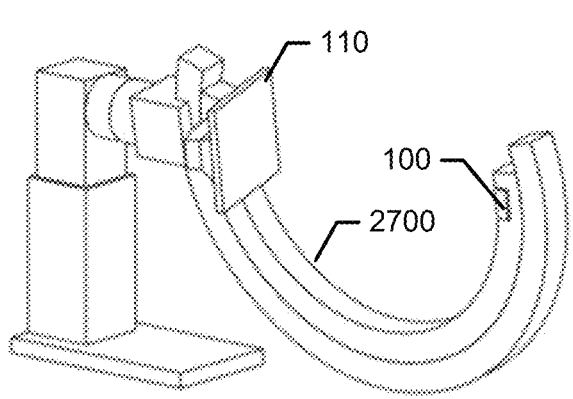
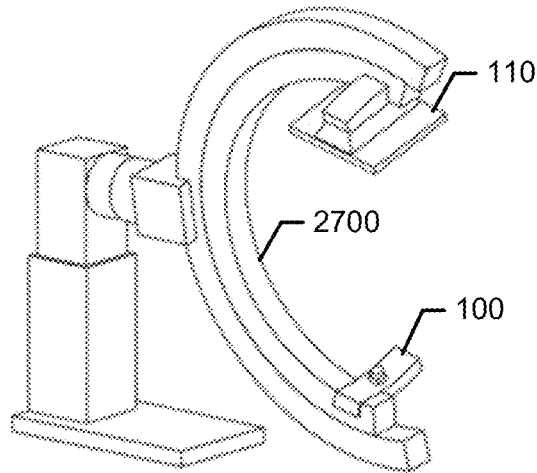
FIGURE 27a  FIGURE 27b
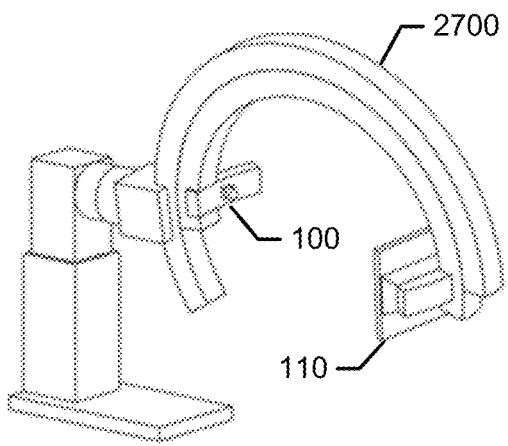
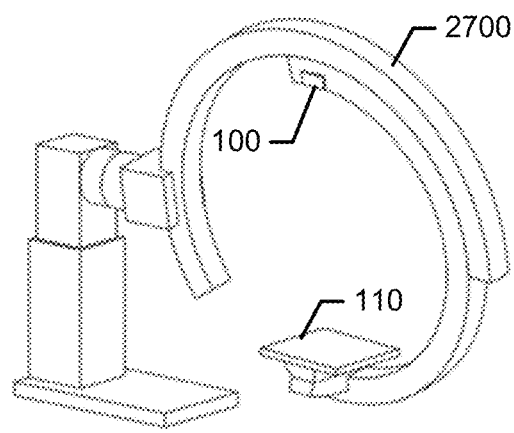
FIGURE 27c  FIGURE 27d

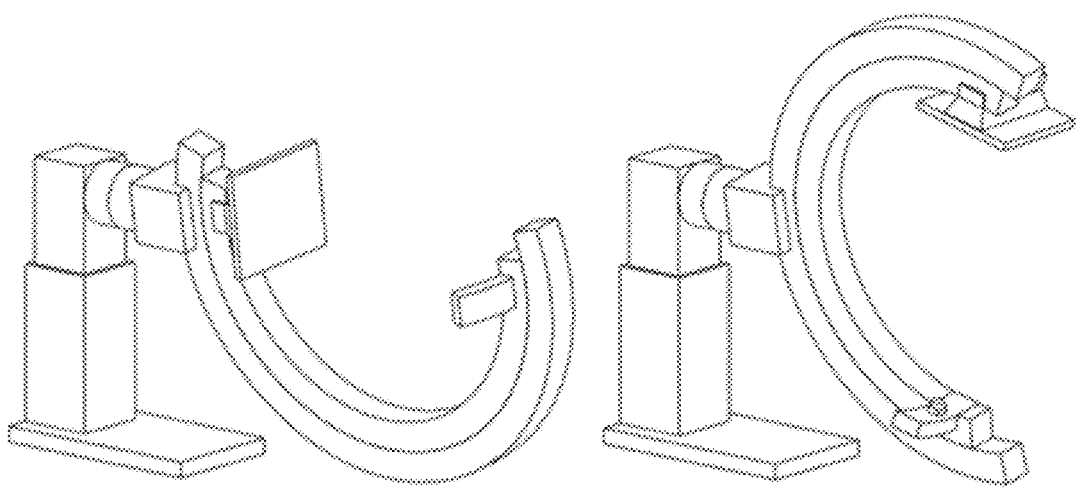
FIGURE 28a  FIGURE 28b
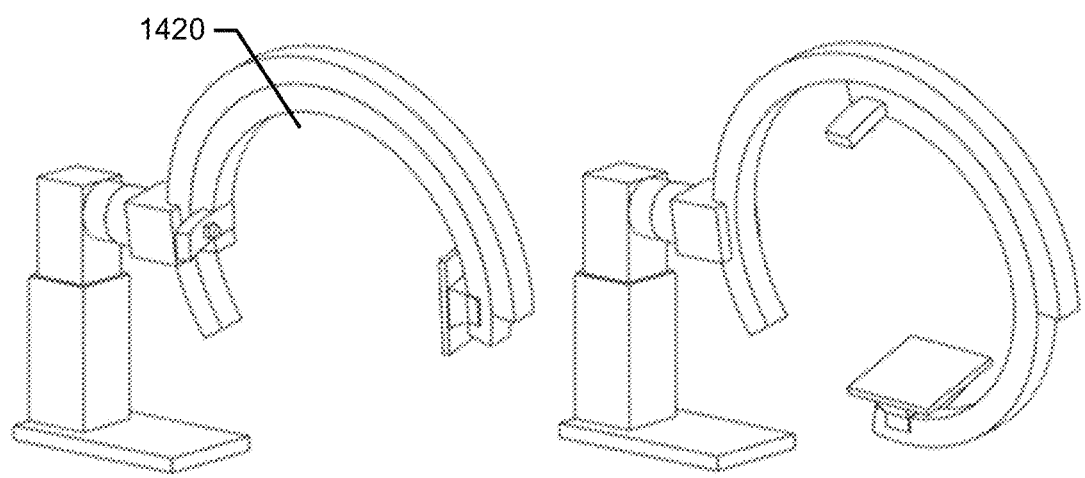
FIGURE 28c  FIGURE 28d

INCREASED CONE BEAM COMPUTED TOMOGRAPHY VOLUME LENGTH WITHOUT REQUIRING STITCHING OR LONGITUDINAL C-ARM MOVEMENT

TECHNICAL FIELD

The present disclosure relates to medical imaging systems, and more particularly, controlled movement of the imaging system or components thereof.

BACKGROUND OF THE DISCLOSURE

Healthcare practices have shown the tremendous value of three-dimensional imaging such as computed tomography (CT) imaging, as a diagnostic tool in the Radiology Department. These imaging systems generally contain a fixed bore into which the patient enters from the head or foot. Other areas of care, including the operating room, intensive care departments and emergency departments, rely on two-dimensional imaging (fluoroscopy, ultrasound, 2-D mobile X-ray) as the primary means of diagnosis and therapeutic guidance.

While mobile solutions for 'non-radiology department' and patient-centric 3-D imaging do exist, they are often limited by their freedom of movement to effectively position the system without moving the patient. Their limited freedom of movement has hindered the acceptance and use of mobile three-dimensional imaging systems.

Therefore, there is a need for a small scale and/or mobile three-dimensional imaging systems for use in the operating room, procedure rooms, intensive care units, emergency departments and other parts of the hospital, in ambulatory surgery centers, physician offices, and the military battlefield, which can access the patients in any direction or height and produce high-quality three-dimensional images. These imaging systems may include intra-operative CT and magnetic resonance imaging (MM) scanners, and robotic systems to aid in their use or movement. These include systems with 180-degree movement capability ("C-arms") and may also include imaging systems with 360-degree movement capability ("O-arms").

Some three-dimensional imaging systems expose patients to substantial non-uniform radiation dosages, which affects imaging clarity, and may require longitudinal movements of the imaging device to separately image different sections of the desired volumes and then use computationally complex operations to attempt to stitch together those scan volumes. A related complication when attempting to image spaced scan volumes is how to precisely reposition the imaging system. Image stitching can be especially difficult in an operating room or operating theatre, where the size and weight of the imaging equipment and the presence of numerous required personnel make it difficult to precisely reposition the imaging equipment.

SUMMARY OF THE DISCLOSURE

Some embodiments of the present disclosure are directed to a medical imaging system that includes a movable station having a C-arm, an X-ray collector, an X-ray beam emitter, and a controller. The C-arm has a first end and a second end that are movable along an arc relative to the movable station. The collector is attached to the first end of the C-arm. The X-ray beam emitter faces the collector to emit an X-ray beam in a direction of the collector and is attached to the second end of the C-arm. The controller is configured to move one of the X-ray beam emitter and the collector to a first offset position relative to each other along a lateral axis orthogonal to the arc. The controller obtains a first set of images by rotating the collector and the X-ray beam emitter along the arc about a scanned volume while the X-ray beam emitter and the collector are positioned with the first offset position. The controller moves the one of the X-ray beam emitter and the collector to a second offset position relative to each other along the lateral axis orthogonal to the arc. The controller obtains a second set of images by rotating the collector and the X-ray beam emitter along the arc about the scanned volume while the X-ray beam emitter and the collector are positioned with the second offset position. The controller combines the first and second set of images to generate a three-dimensional image of the scanned volume.

Some other embodiments of the present disclosure are directed to another medical imaging system that includes a movable station having a C-arm, a collector, two X-ray beam emitters, and a controller. The C-arm has a first end and a second end that are movable along an arc relative to the movable station. The collector is attached to the first end of the C-arm. A first X-ray beam emitter and a second X-ray beam emitter both face the collector to emit X-ray beams in a direction of the collector and both are attached to the second end of the C-arm. The collector and the first and second X-ray beam emitters are spaced apart relative to each other along a lateral axis orthogonal to the arc. The controller is configured to obtain at least one set of images by rotating the collector and the first and second X-ray beam emitters along the arc about a scanned volume, and to combine the at least one set of images to generate a three-dimensional image of the scanned volume.

Some other embodiments of the present disclosure are directed to a computer program product including a non-transitory computer readable medium storing program code executable by at least one processor of a controller of a medical imaging system to perform operations for X-ray imaging. The operations move one of an X-ray beam emitter and a collector to a first offset position relative to each other along a lateral axis orthogonal to an arc. The operations obtain a first set of images by rotating the collector and a X-ray beam emitter along the arc about a scanned volume while the X-ray beam emitter and the collector are positioned with the first offset position. The operations move the one of the X-ray beam emitter and the collector to a second offset position relative to each other along the lateral axis orthogonal to the arc. The operations obtain a second set of images by rotating the collector and the X-ray beam emitter along the arc about the scanned volume while the X-ray beam emitter and the collector are positioned with the second offset position. The operations combine the first and second set of images to generate a three-dimensional image of the scanned volume.

It is noted that aspects described with respect to one embodiment disclosed herein may be incorporated in different embodiments although not specifically described relative thereto. That is, all embodiments and/or features of any embodiments can be combined in any way and/or combination. Moreover, methods, systems, and/or computer program products according to embodiments will be or become apparent to one with skill in the art upon review of the following drawings and detailed description. It is intended that all such additional methods, systems, and/or computer program products be included within this description and protected by the accompanying claims.

BRIEF DESCRIPTION OF DRAWINGS

Aspects of the present disclosure are illustrated by way of example and are not limited by the accompanying drawings. In the drawings:

FIGS. 27a-d illustrate four views of the C-arm rotating the collector and X-ray beam emitter along an arc while the collector and X-ray beam emitter are rotated +9.4 degrees distal to the other rotations during the spin.

FIGS. 28a-d illustrate four view of the C-arm rotating the collector and X-ray beam emitter along an arc while the collector and X-ray beam emitter are rotated −9.4 degrees distal to the other rotations during the spin.

DETAILED DESCRIPTION

Figure 1:
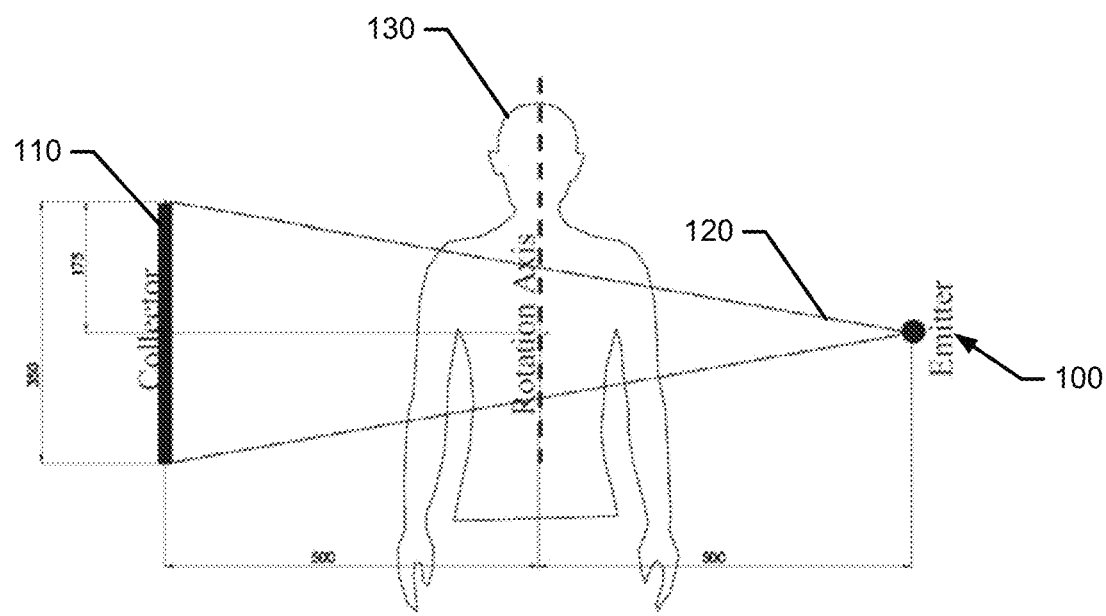
FIG. 1 illustrates components of a traditional imaging system including an X-ray beam emitter emitting a beam to a collector rotating about a patient on a rotation axis.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

For purposes of this application, the terms "code", "software", "program", "application", "software code", "software module", "module" and "software program" are used interchangeably to mean software instructions that are executable by a processor. A "user" can be a physician, nurse, or other medical professional.

Turning now to the drawing, FIG. 1 illustrates components of a traditional imaging system including an X-ray beam emitter 100 emitting a beam 120 to a collector 110 rotating about a patient 130 on a rotation axis. The X-ray beam emitter 100 is mounted to one end of a C-arm while an imaging sensor such as the collector 110 is mounted to the other end of the C-arm and faces the X-ray beam emitter. A motor attached to a vertical shaft of the C-arm is designed to rotate the collector 110 and X-ray beam emitter 100 up to 360 degrees about the rotational axis under the control of a controller. In this example, the X-ray beam emitter 100 transmits an X-ray beam 120 which is received by collector 110 after passing through a relevant portion of a patient 130.

An example C-arm including an X-ray emitter and collector is illustrated FIGS. 26, 27*a-d*, and 28-*a-d*.

It may be desirable to take X-rays of patient 130 from a number of different positions, without the need for frequent manual repositioning of patient 130 which may be required in an X-ray system. The medical imaging system may be in the form of a C-arm that includes an elongated C-shaped member terminating in opposing distal ends of the "C" shape. The space within C-arm of the arm may provide room for the physician to attend to the patient substantially free of interference from X-ray support structure.

The image capturing components include the X-ray beam emitter 100 and the collector 110, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 130 to be acquired from multiple directions or in multiple planes.

The images collected while the C-arm rotates the collector 110 and X-ray beam emitter 100 around the patient 130 are then combined to generate a three-dimensional image of a scanned volume. When a 3D reconstruction from a cone beam 120 is produced, the volume is limited by what can be captured by the X-ray path. For example, a collector may be 35 cm across and spacing between emitter and collector may be 1 m, such as shown in FIG. 1.

Figure 2:
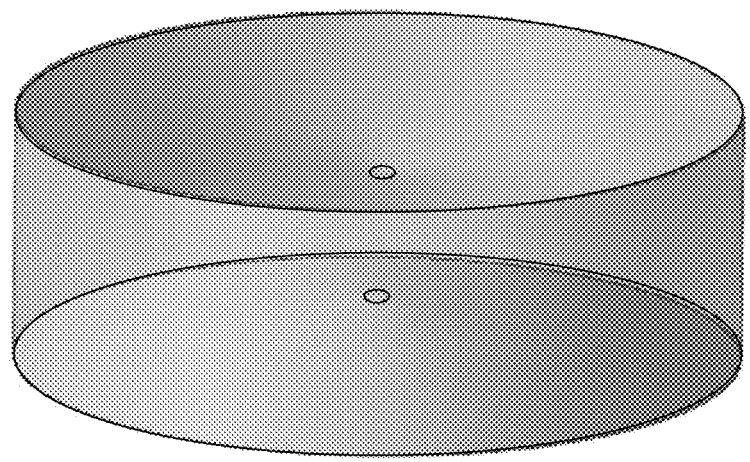
FIG. 2 illustrates a 3D volume created by performing an image scan while rotating about a fixed axis and back projecting the obtained set of images.

FIG. 2 illustrates a 3D image volume created by performing an image scan while rotating about a fixed axis and back projecting the obtained set of images. Because of how the cone beam, which is triangular in cross-section, is swept about the rotation axis 130, this 3D image volume constructed by back projecting is generally cylindrical in shape, but with inward facing conical voids at the top and bottom ends of the cylinder, which is where x-ray beams do not pass.

Figure 3:
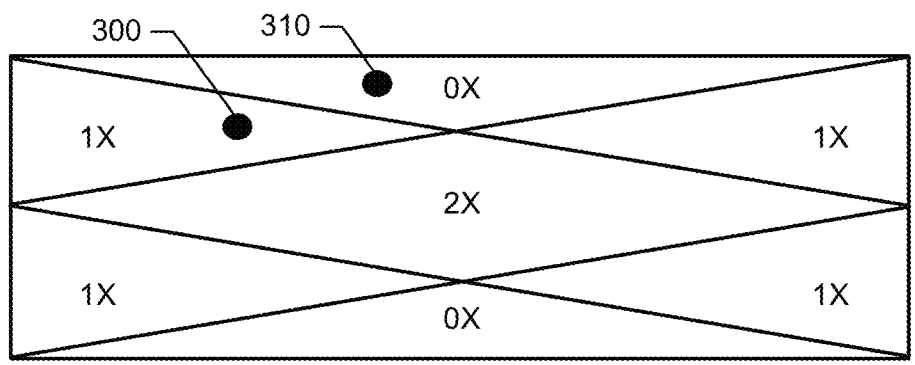
FIG. 3 illustrates substantial non-uniform radiation dosages of the imaging volume.

FIG. 3 illustrates a two-dimensional side perspective of the image volume illustrated in FIG. 2. Some parts of the patient anatomy toward the edges are only penetrated by X-rays during certain perspectives. Therefore, the image reconstruction is less robust. For example, anatomy located at 300 is not struck by X-rays from left to right but is struck from right to left. Other anatomy is never intersected, such as anatomy located at point 310. The regions of FIG. 3 are labeled 0×, 1×, or 2×, meaning they are intersected by X-rays not at all (0×), not from all perspectives (1×) or from all perspectives (2×). Unnecessary and/or inefficient use of radiation should be avoided when imaging a patient, so regions not intersected by X-rays or not intersected from all perspectives should try to be avoided or minimized.

Figure 4:
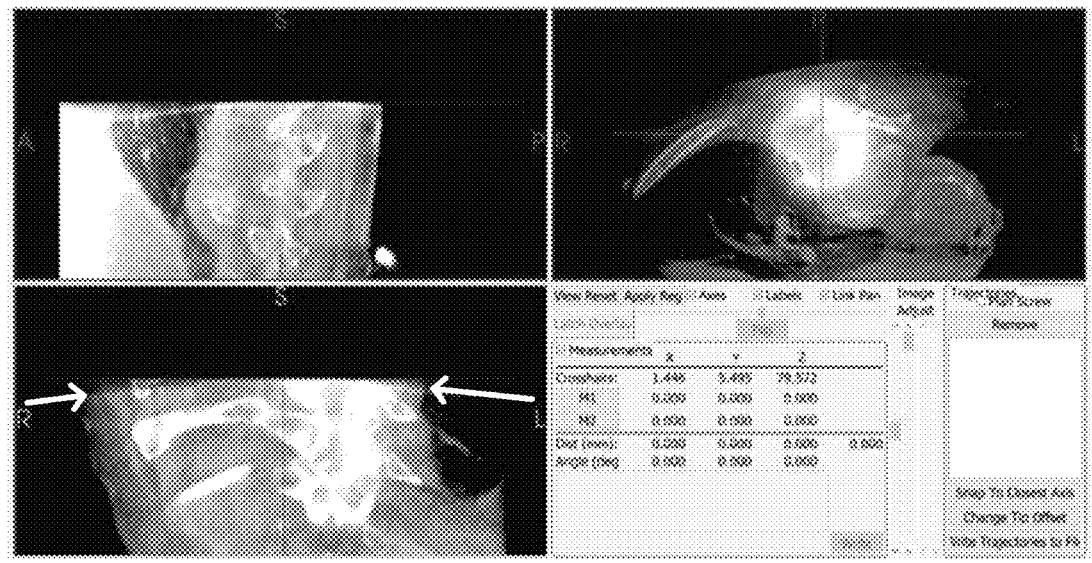
FIG. 4 illustrates a Cone Beam Computed Tomography, CBCT, scan volume.

FIG. 4 illustrates an example cone beam computed tomography, CBCT, scan volume. Note the white halo on the axial view where the scan reaches its limit of visibility of the scanned anatomy, and simultaneously, the other views show the darker regions where tissues are intersected from only a subset of perspectives. White lines in the bottom left image are overlaid where the boundary from 1× to 2× as described in FIG. 3 occurs.

Because the region of interest is only in the "2×" area, the height of the cylindrical scan volume is reduced compared to the height of the collector. In the illustrated example, the height of the 2× region is 175 mm, which is 50% of the collector height.

Figure 5:
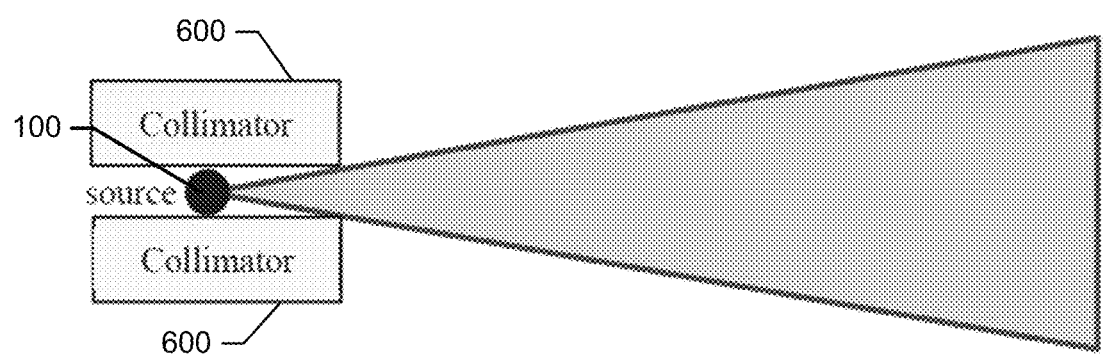
FIG. 5 illustrates a configuration of collimators to limit the X-rays to a triangular strip of interest for acquiring a scan volume such as shown in the earlier figures.

CBCT devices place a metal (lead) barrier or collimator around the emitter to prevent excessive irradiation of the patient. However, the collimation occurs on the side of the emitter, so unwanted X-rays still extend above and below the region of interest. For example, FIG. 5 illustrates a configuration of collimators 600 to limit the X-rays to triangular strip of interest for acquiring the scan volume of the earlier figures.

The X-ray beam emitter contains a collimator 600 that forms a window which shapes an X-ray beam transmitted therethrough toward the collector. The collimator 600 is configured to move a location of the widow in a lateral direction across the arc direction. A controller is configured to control movement of the window by the collimator 600 to steer the X-ray beam laterally across the collector in accordance with some embodiments.

In some embodiments, a collimator 600 is used to adjust the size and/or lateral location of the X-ray beam, e.g., relative to the direction of the arcuate image scan.

The collimator 600 includes a pair of shutters (not shown) that are on opposite sides of a window, in accordance with some embodiments. The shutters are formed from a material, such as lead, that substantially blocks X-rays. Motor mechanisms are connected to slide a respective one of the shutters along tracks extending in the lateral direction to change the locations of opposing edges of the window. The controller controls the motor mechanisms to set the lateral distance between the shutters to control width of the X-ray beam, and further controls the motor mechanisms to move the window to steer the X-ray beam across the collector.

Figure 6:
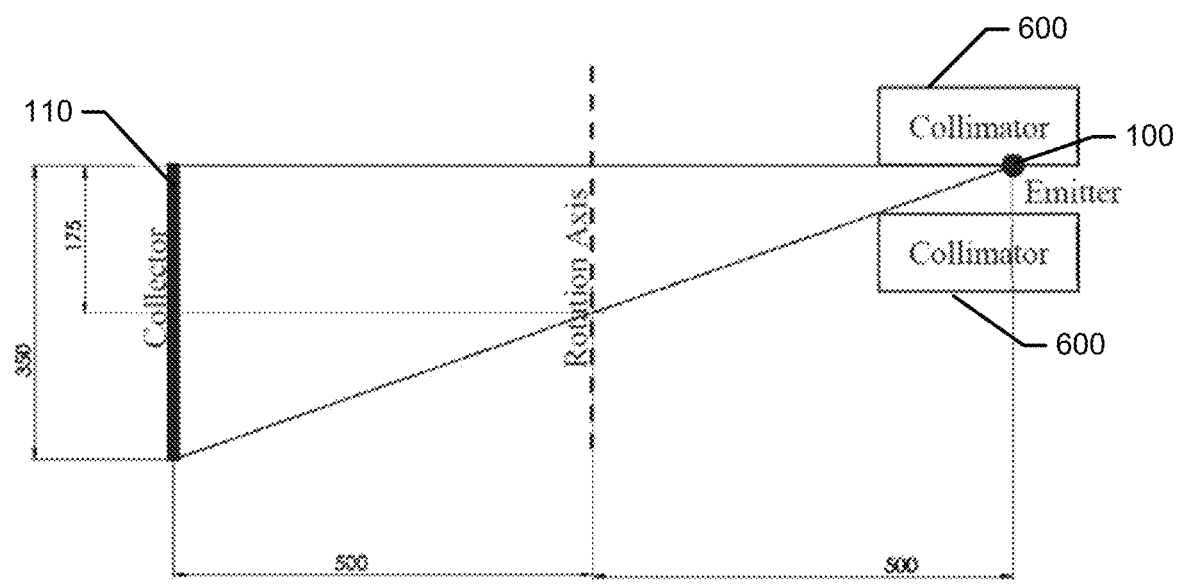
FIG. 6 illustrates the X-ray beam emitter lateral offset in a first direction relative to the collector of a medical imaging system while performing an image scan to generate a first set of images according to some embodiments of the present disclosure.

FIG. 6 illustrates the X-ray beam emitter 100 positioned laterally offset in a first direction relative to the collector 110 of a medical imaging system to be roughly in line across the x-ray path with the top of the collector while being rotated about the rotational axis along an arc to perform an image scan to generate a first set of images according to some embodiments of the present disclosure.

Figure 7:
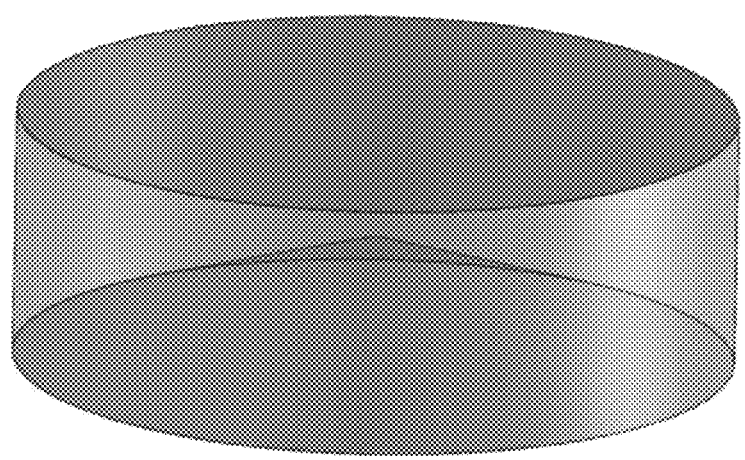
FIG. 7 illustrates a reconstruction of the image volume that may be created by the medical imaging system configured according to FIG. 6.

FIG. 7 illustrates the reconstruction of the image volume that may be created by the image scan performed while the medical imaging system is configured as shown in FIG. 6. Because of how the cone beam, which is triangular in cross-section, is swept about the rotation axis 130, this 3D image volume constructed by back projecting is generally cylindrical in shape, but with one inward facing conical void at the bottom end of the cylinder, which is where x-ray beams do not pass.

Figure 8:
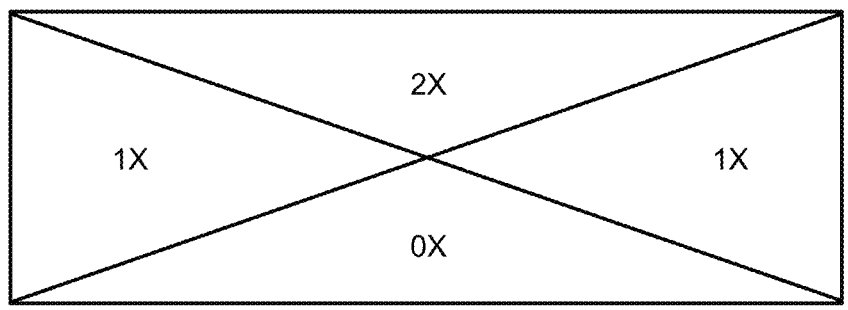
FIG. 8 illustrates a two-dimensional side perspective of the image volume created by the medical imaging system configured according to FIG. 6.

FIG. 8 illustrates the two-dimensional side perspective of the image volume created by the image scan performed while the medical imaging system is configured as shown in FIG. 6. As with the case where the emitter is centered (FIG. 3) instead of laterally offset, there are regions of 0×, 1×, and 2×; however, with the emitter offset in a first direction, these regions are differently spatially distributed than in the centered case.

Figure 9:
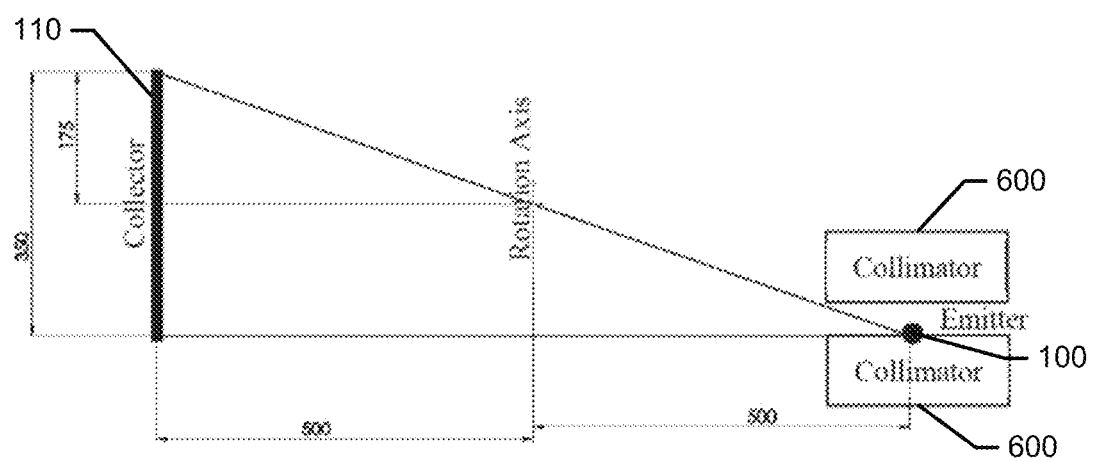
FIG. 9 illustrates the X-ray beam emitter lateral offset in an opposite second direction relative to the collector of the medical imaging system while performing an image scan to generate a second set of images according to some embodiments of the present disclosure.

FIG. 9 illustrates the X-ray beam emitter 100 laterally offset in an opposite second direction relative to the collector 110 of the medical imaging system to be roughly in line across the x-ray path with the bottom of the collector while performing an image scan to generate a second set of images according to some embodiments of the present disclosure.

Figure 10:
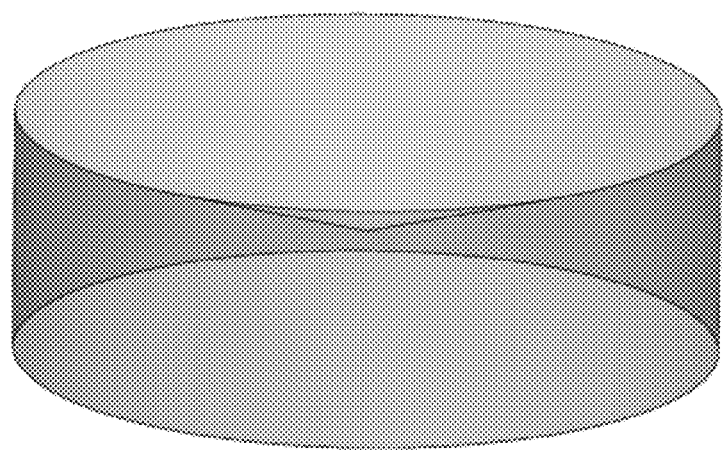
FIG. 10 illustrates a reconstruction of the image volume that may be created by the medical imaging system configured according to FIG. 9.

FIG. 10 illustrates the reconstruction of the image volume that may be created by the image scan performed while the medical imaging system is configured according to FIG. 9. Because of how the cone beam, which is triangular in cross-section, is swept about the rotation axis 130, this 3D image volume constructed by back projecting is generally cylindrical in shape, but with one inward facing conical void at the top end of the cylinder, which is where x-ray beams do not pass.

Figure 11:
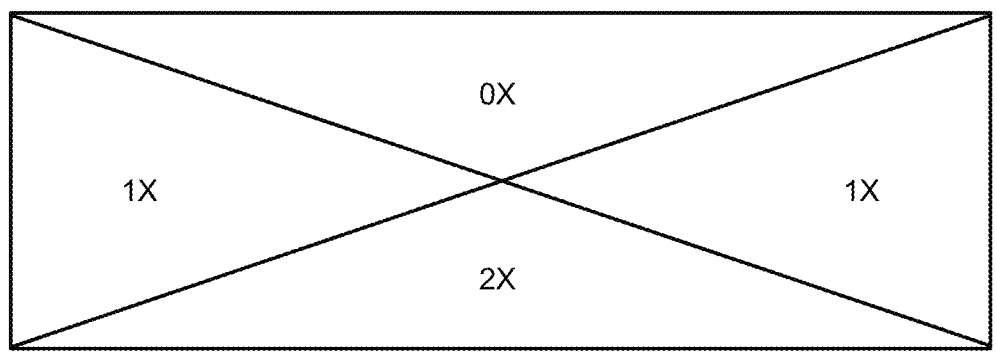
FIG. 11 illustrates a two-dimensional side perspective of the image volume created by the medical imaging system configured according to FIG. 9.

FIG. 11 illustrates the two-dimensional side perspective of the image volume created by the image scan performed while the medical imaging system is configured according to FIG. 9. As with the case where the emitter is positioned centered (FIG. 3) instead of laterally offset, there are regions of 0×, 1×, and 2×; however, with the emitter offset in a second direction, these regions are differently spatially distributed than in the centered case and inversely to the case where the emitter is offset in a first direction (FIG. 8).

Figure 12:
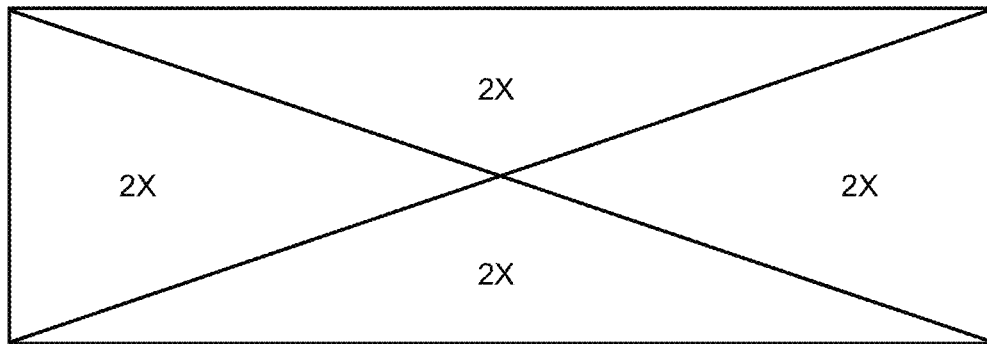
FIG. 12 illustrates a two-dimensional side perspective of the image volume created by the combination of the first and second set of scan volumes of FIGS. 9 and 12 in accordance with some embodiments of the present disclosure.

FIG. 12 illustrates a two-dimensional side perspective of the image volume created by the combination (overlap) of the first and second set of scan volumes of FIGS. 9 and 12 in accordance with some embodiments of the present disclosure. The image volume is cylindrical with the same height as the height of the collector 110. Note how consistent the dosage is in every part of the scan (2×). The regions in all areas are penetrated by X-rays from all perspectives. There are no 1× regions at the top or bottom of the cylinder, in sharp contrast to the image volumes shown in FIGS. 7 and 10. This uniformity is because the top and bottom regions are penetrated at 2× by the individual scans and the regions to left and right are penetrated at 1× each, so when summed, they all penetrate at 2×.

Figure 13:
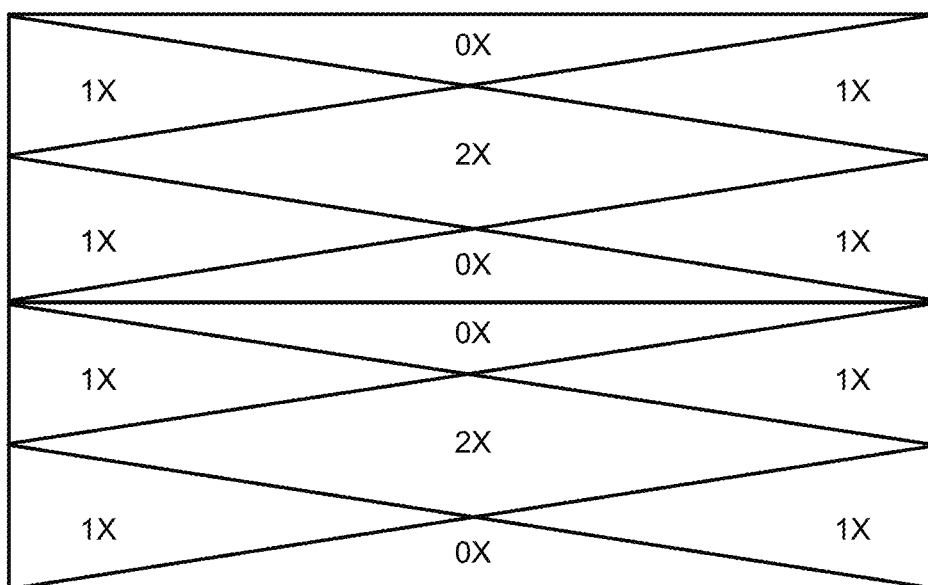
FIG. 13 illustrates traditionally configured longitudinally offset image volumes that are stitched together, end to end.
Figure 14:
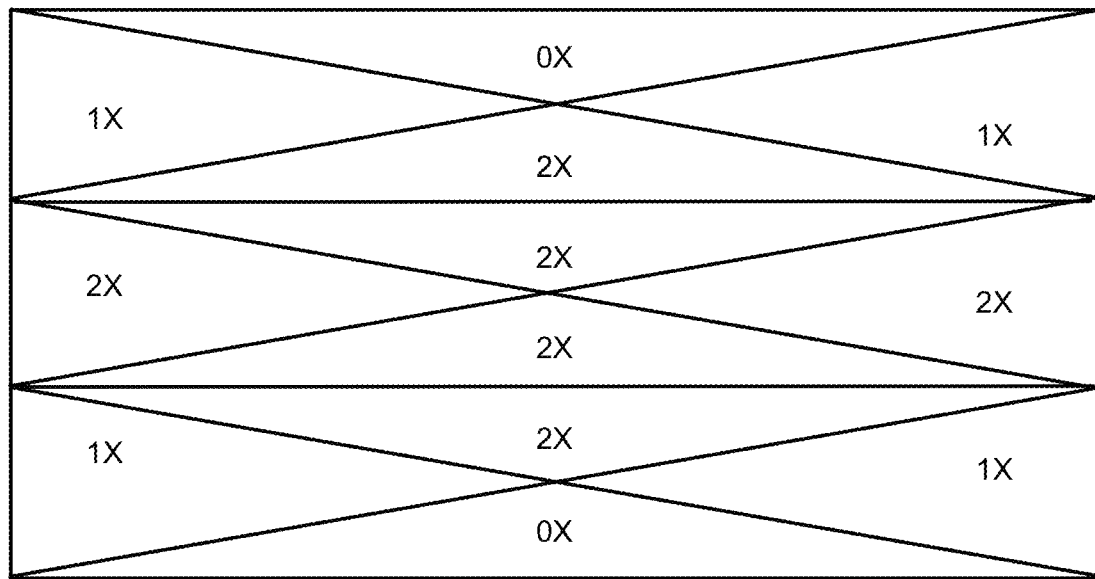
FIG. 14 illustrates traditionally configured image volumes stitched together with the corners of the 2× regions opposed to one another.

For comparison with the above embodiment, consider taking two longitudinally offset image volumes according to the traditional configuration of the X-ray beam emitter 100 centered on the collector 110 (as illustrated in FIG. 1) and stitching them together, end to end. FIG. 13 illustrates these traditionally configured longitudinally offset image volumes stitched together, end to end. The image volumes cannot be stitched exactly end to end because of the suboptimal X-ray penetration conditions at the ends of each volume. Instead, the corners of the 2× regions would need to be apposed to one another, as illustrated in FIG. 14. In this case, the combined image volume has the same working height as in the modified method, but there is less consistent penetration of all regions and there is unwanted and unused penetration of X-rays beyond either end of the image volume, which means the patient would receive a greater X-ray dose if images acquired by the traditional configuration were stitched than if some embodiments of the present disclosure were used. Although stacking images end to end would result in an image twice as long, it would require the entire X-ray apparatus (collector and X-ray beam emitter) to be moved longitudinally by ½ the collector height, in contrast with some embodiments of the present disclosure, in which only the emitter is moved.

Figure 15:
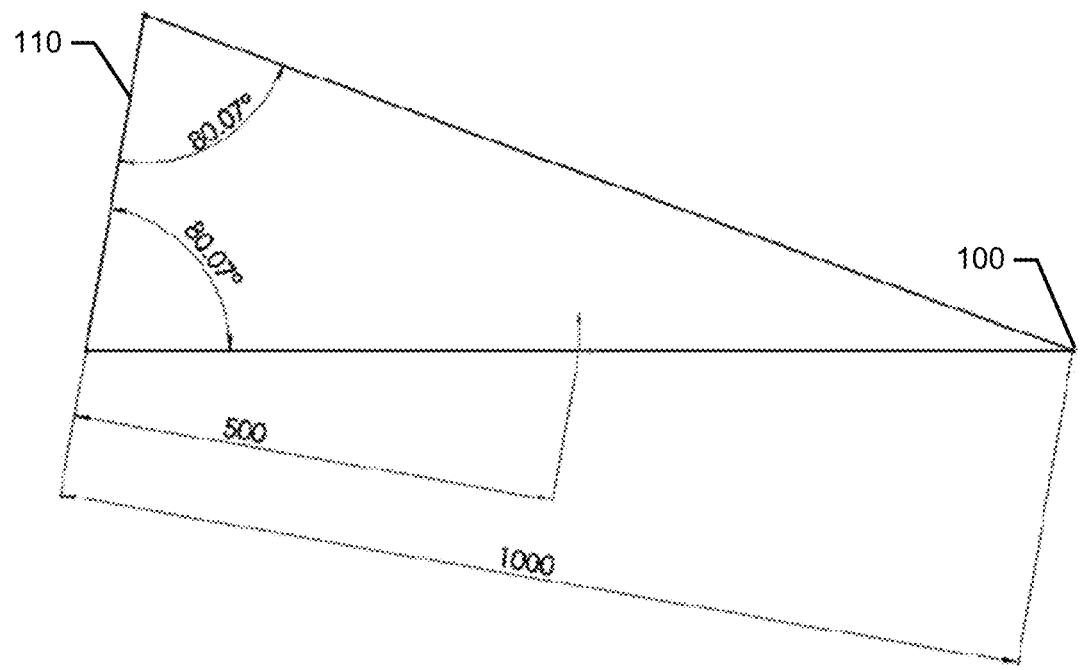
FIG. 15 illustrates an example configuration of the X-ray beam emitter angled up while performing an image scan to generate a first set of images in accordance with some embodiments of the present disclosure.

In some other embodiments of the present disclosure, the X-ray beam emitter and collector can be angled up and down during image scans. FIG. 15 illustrates an example configuration of the X-ray beam emitter 100 angled up while performing an image scan to generate a first set of images in accordance with some embodiments of the present disclosure.

Figure 16:
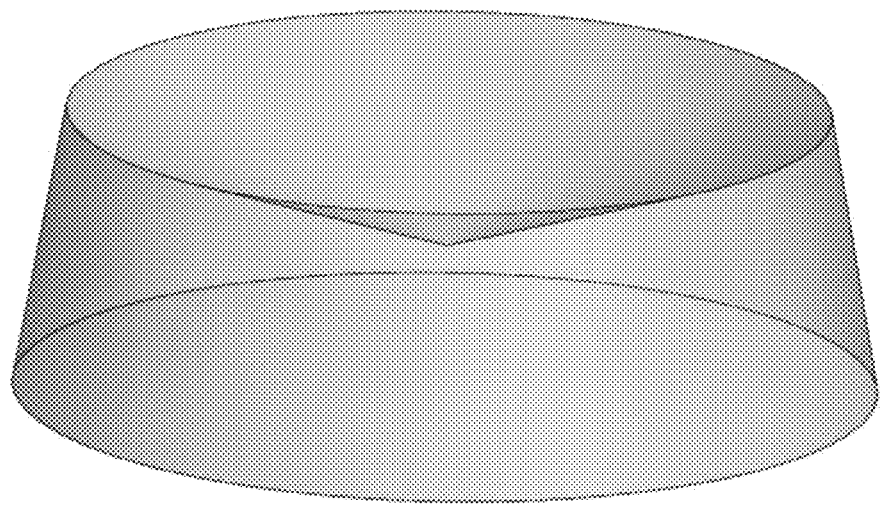
FIG. 16 illustrates a reconstruction of the image volume created by performing an image scan with the X-ray beam emitter angled up as shown in FIG. 15.

FIG. 16 illustrates the reconstruction of the image volume created by performing an image scan with the X-ray beam emitter angled up as shown in FIG. 15. This image volume is shaped like a pet food bowl—flat on the bottom and tapered on the sides, with a conical void on the top where x-rays do not pass.

Figure 17:
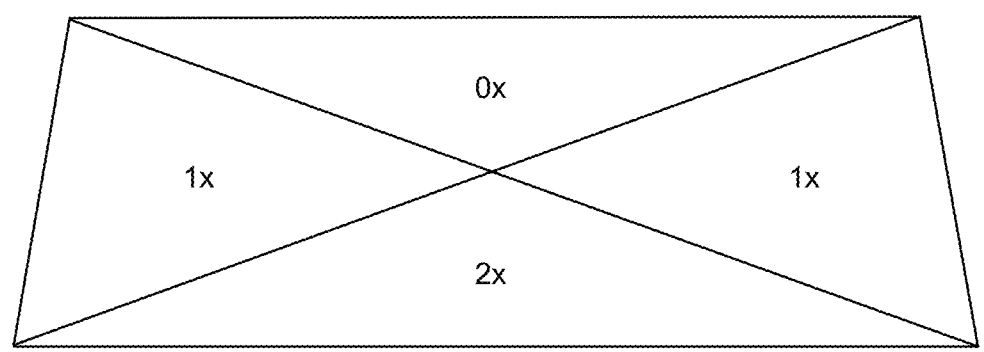
FIG. 17 illustrates a two-dimensional side perspective of an image volume created by the medical imaging system configured as shown in FIG. 15.

FIG. 17 illustrates the two-dimensional side perspective of the image volume created by the medical imaging system configured as shown in FIG. 15.

Figure 18:
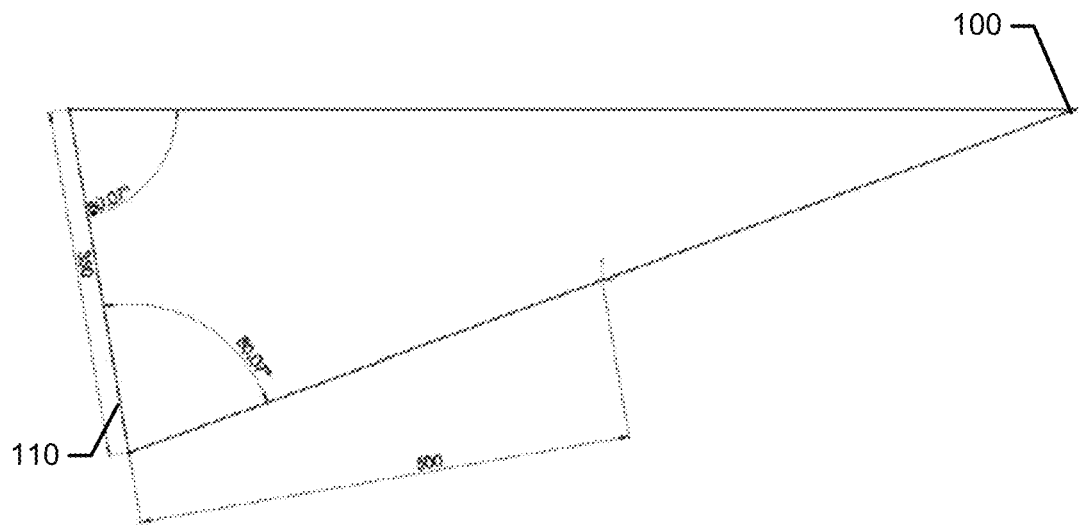
FIG. 18 illustrates an example configuration of the X-ray beam emitter angled down while performing a second image scan to generate a second set of images in accordance with some embodiments.

FIG. 18 illustrates an example configuration of the X-ray beam emitter angled down while performing a second image scan to generate a second set of images in accordance with some embodiments.

Figure 19:
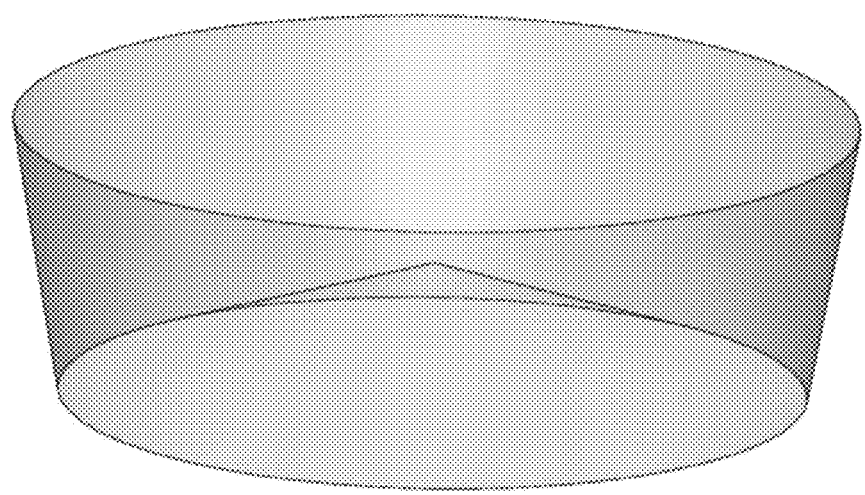
FIG. 19 illustrates a reconstruction of the image volume created by the medical imaging system when configured as shown in FIG. 18.

FIG. 19 illustrates the reconstruction of the image volume created by the medical imaging system when configured as shown in FIG. 18. The 3D shape of this image volume is the inverse of that shown in FIG. 16.

Figure 20:
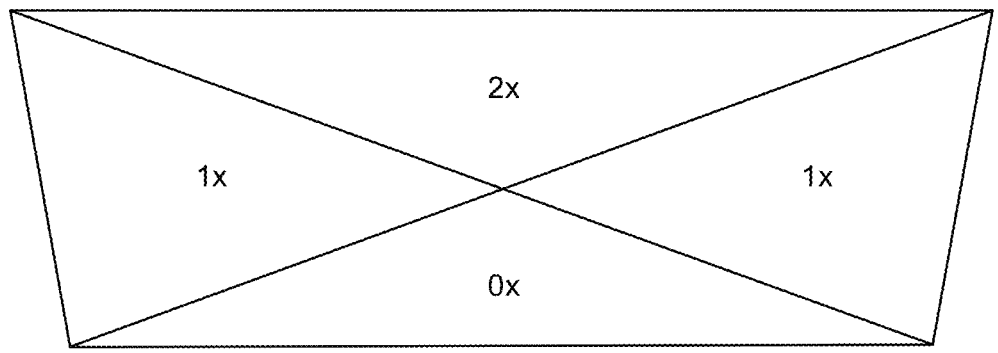
FIG. 20 illustrates a two-dimensional side perspective of the volume created by the medical imaging system when configured as shown in FIG. 18.

FIG. 20 illustrates the two-dimensional side perspective of the volume created by the medical imaging system when configured as shown in FIG. 18.

Figure 21:
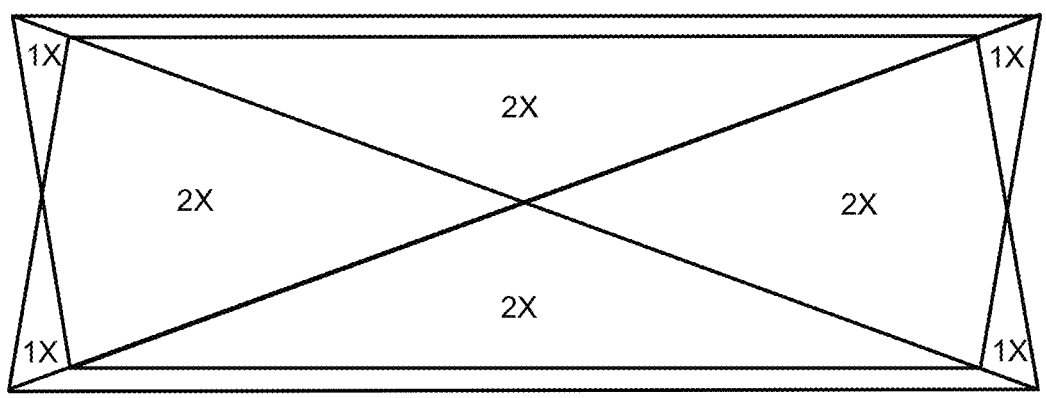
FIG. 21 illustrates the two-dimensional side perspective of the volume created by the combination of the first and second set of images from the image scans of FIGS. 16-18 and then FIGS. 18-20.

FIG. 21 illustrates the two-dimensional side perspective of the volume created by the combination of the first and second set of images from the image scans of FIGS. 16-18 and then FIGS. 19-21. The combined volumes slightly exceed the collector height. In this example, the angle difference is 19.86☐, so just tilting the emitter-collector assembly up 9.4☐ and down 9.4☐ doubles the image volume. Combination of volumes in this embodiment can provide similar advantages over the stitching of 2 standard images: there is less unused radiation at either end of the scan and the volume is essentially doubled with no longitudinal movement of the machine, just a slight angulation.

In various embodiments of the present disclosure, a different method can be used to generate CBCT reconstructions by: (1) moving the emitter to two or more different offset locations while keeping the collector in a fixed location; (2) using 2 emitters separated by the height of the collector and phasing them; (3) moving the emitter and collector to two or more different perspective angles; or (4) moving the collector in a first direction and C-arm unit in a second (opposite) direction to two or more different offset positions while keeping the emitter fixed relative to the unit and the anatomical scan region fixed relative to the patient.

In some embodiments of the present disclosure, the X-ray beam emitter can be moved in an offset direction to one or more additional position other than the two positions illustrated in FIGS. 6, 9, 15, and 18 and additional scan volumes collected and combined with the scans already combined. For example, three scans can be collected in each of three emitter positions shown in FIG. 22. By further combining additional positions, the image quality may be improved and transitional regions represented by the diagonal lines on FIGS. 12 and 21 may have less artifact. Additional scans may be obtained at lower X-ray power to avoid unnecessarily dosing the patient.

Figure 22:
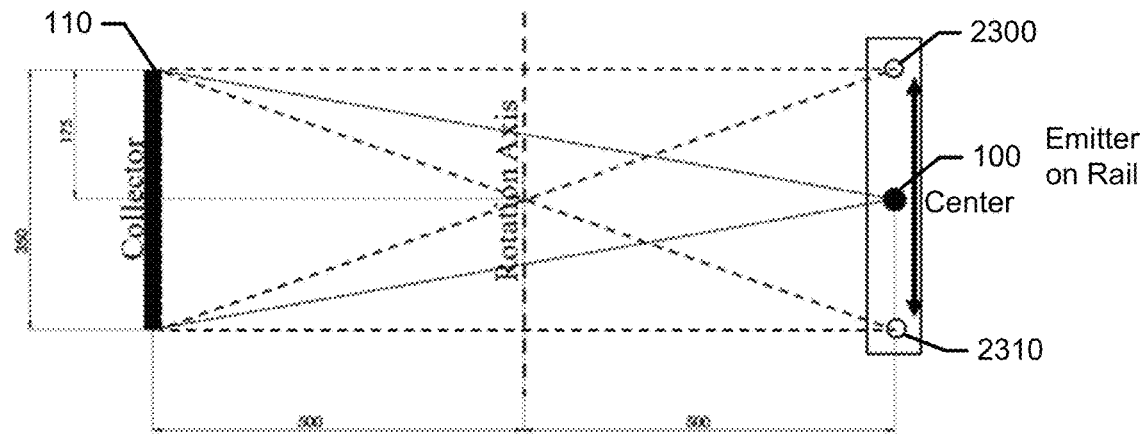
FIG. 22 illustrates the X-ray beam emitter configured to be moveable along a linear rail attached to the second end of the C-arm in accordance with some embodiments of the present disclosure.
Figure 23:
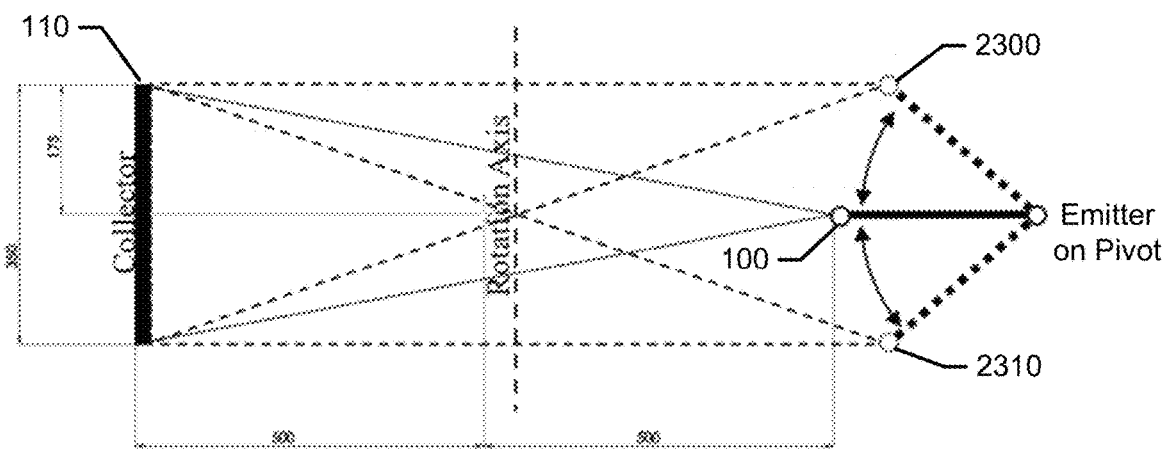
FIG. 23 illustrates the X-ray beam emitter configured to be moveable about an angular pivot attached to the second end of the C-arm in accordance with some embodiments of the present disclosure.

In some embodiments, the medical imaging system is contemplated that has an X-ray beam emitter 100 on a moving platform to shift it to be in line with either the top, middle, or bottom of the collector 110. FIG. 22 illustrates the mechanism moving the X-ray beam emitter on a linear rail. FIG. 23 illustrates the mechanism moving (angularly rotating) the X-ray beam emitter on a pivot. If positioned at the center position, the system would operate traditionally. In the first offset position 2300 and the second offset position 2310, two separate scans would be taken and would be combined for a double-length scan volume.

Figure 32:
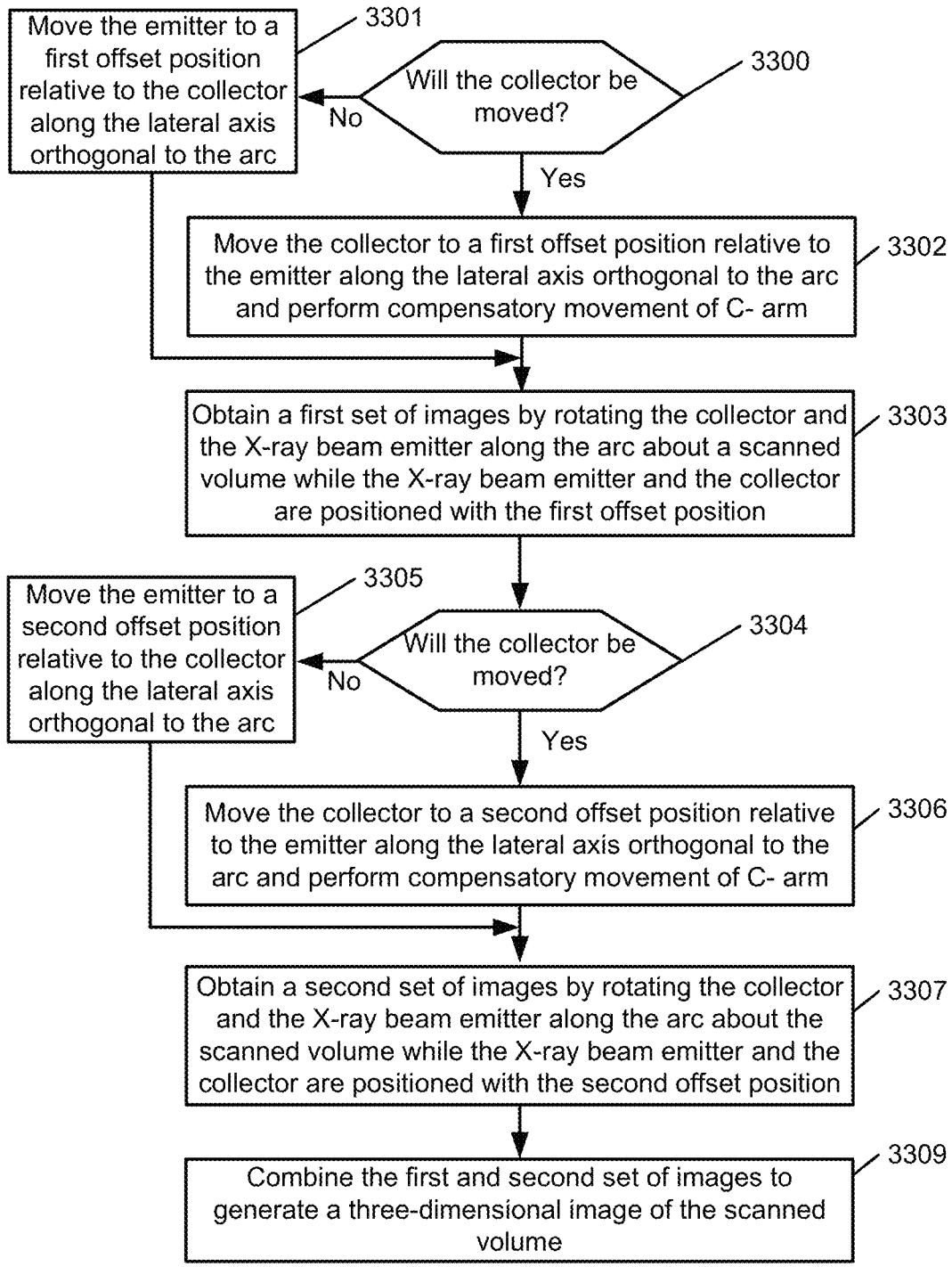
FIG. 32 and FIG. 33 are flowcharts of operations by a controller of a medical imaging system in accordance with some embodiments of the present disclosure.
Figure 33:
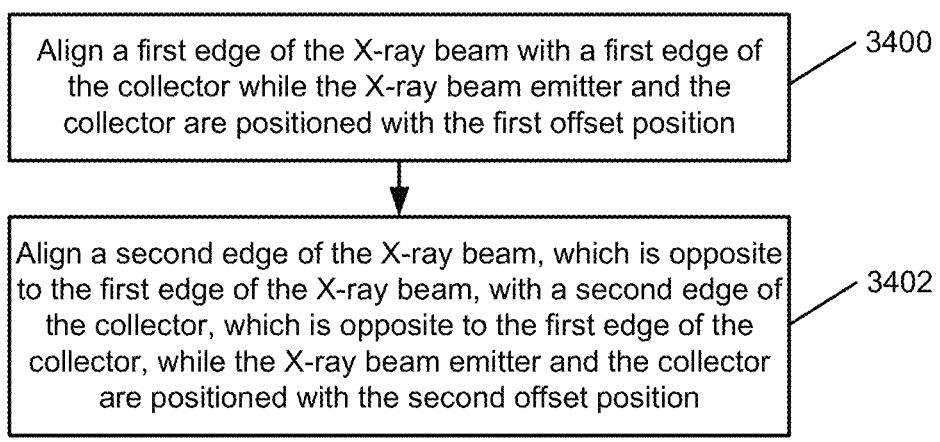

FIG. 32 and FIG. 33 illustrate flowcharts of operations by a controller in accordance with some embodiments of the present disclosure.

Figure 29:
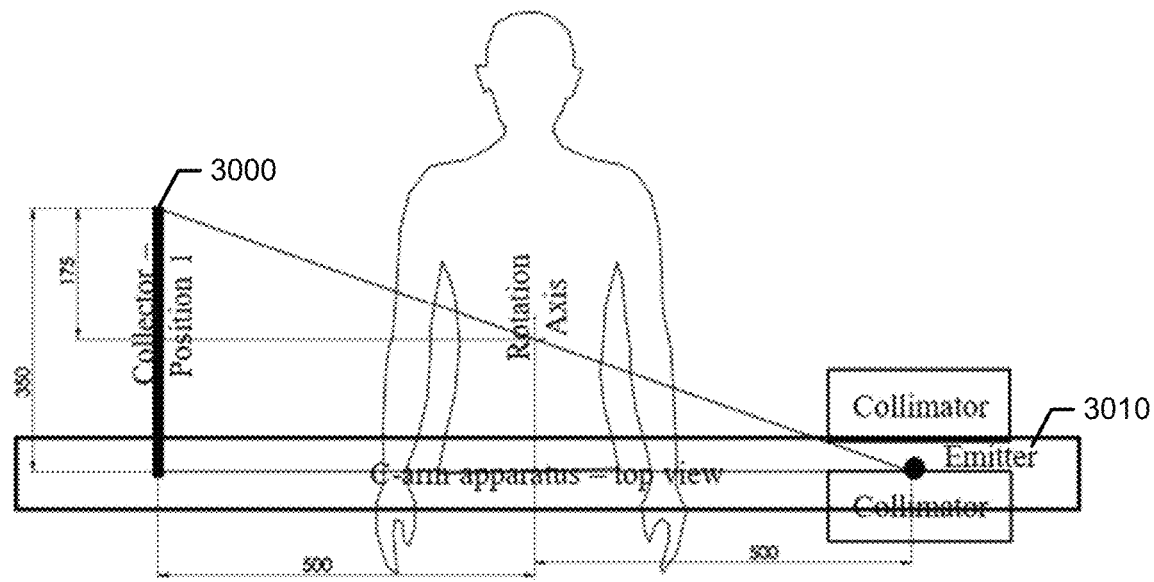
FIG. 29 illustrates the collector in a first laterally offset position in accordance with some embodiments of the present disclosure.

With reference to FIGS. 23, 23, and 32, some embodiments of the present disclosure are directed to a medical imaging system that includes a movable station having a C-arm, a collector 110, an X-ray beam emitter 100, and a controller. The C-arm has a first end and a second end that are movable along an arc relative to the movable station. The collector is attached to the first end of the C-arm. The X-ray beam emitter 100 faces the collector 110 to emit an X-ray beam 120 in a direction of the collector 110 and attached to the second end of the C-arm. A decision 3300 is made whether the collector 110 is to be moved to a first offset position 2300 for imaging. When the decision 3300 is made to not move the collector 110, the emitter 100 is moved 3301 to a first offset position 2300 relative to the collector 110 along the lateral axis orthogonal to the arc. If the emitter 100 moves relative to the collector 110 and C-arm, no movement of the C-arm is required. In contrast, when the decision 3300 is made to move the collector 110, the collector 110 is moved to a first offset position 2300 relative to the emitter 100 along the lateral axis orthogonal to the arc. If the collector 110 moves relative to the emitter 100 and C-arm, a compensatory movement of the C-arm is required to keep the anatomical region of interest centered relative to the collector 110. This compensatory movement is illustrated in FIGS. 28 and 29. The controller obtains 3303 a first set of images by rotating the collector and the X-ray beam emitter 100 along the arc about a scanned volume while at least one of the X-ray beam emitter 100 and the collector 110 is positioned with the first offset position 2300.

Figure 30:
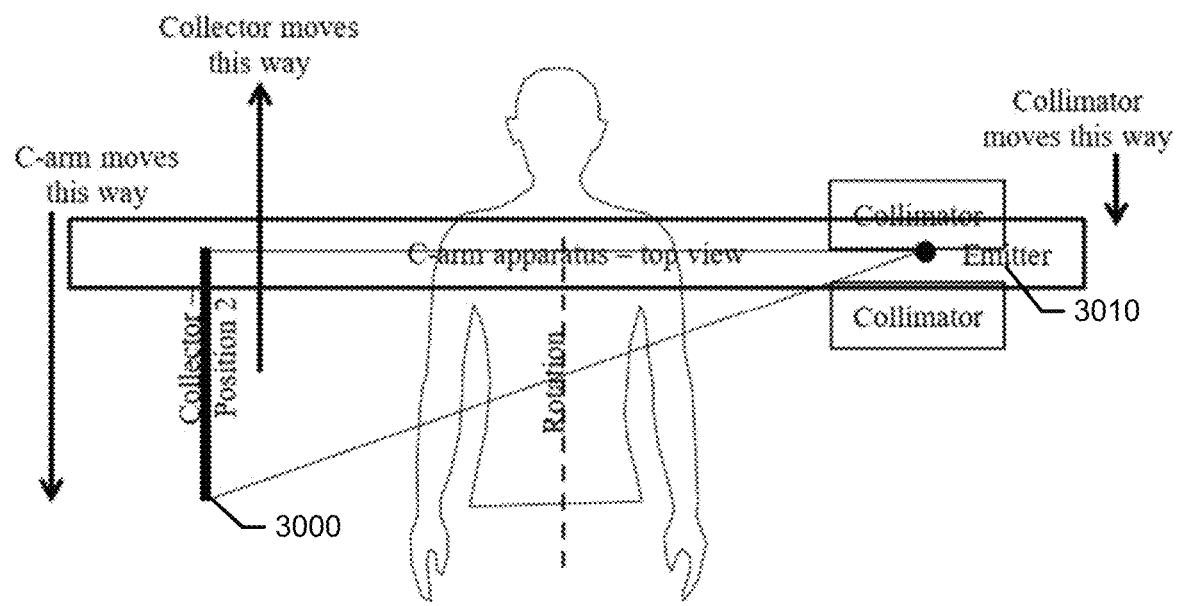
FIG. 30 illustrates the collector in a second laterally offset position in accordance with some embodiments of the present disclosure.

A second decision 3304 is made whether the collector 110 is to be moved to a second offset position 2310 for imaging. When the decision 3304 is made to not move the collector 110, the emitter 100 is moved 3305 to a second offset position 2310 relative to the collector 110 along the lateral axis orthogonal to the arc. In contrast, when the decision 3300 is made to move the collector 110, the collector 110 is moved to a second offset position 2310 relative to the emitter 100 along the lateral axis orthogonal to the arc. If the collector 110 moves relative to the emitter 100 and C-arm, a compensatory movement of the C-arm is required to keep the anatomical region of interest centered relative to the collector 110. This compensatory movement is illustrated in FIGS. 29 and 30. The controller obtains 3306 a second set of images by rotating the collector 110 and the X-ray beam emitter 100 along the arc about the scanned volume while at least one of the X-ray beam emitter 100 and the collector 110 is positioned with the second offset position 2310. The controller combines 3308 the first and second sets of images to generate a three-dimensional image of the scanned volume.

With further reference to FIG. 33, in some embodiments the controller is further configured to align 3400 a first edge of the X-ray beam with a first edge of the collector 110 while the X-ray beam emitter 100 and the collector 110 are positioned with the first offset position 2300. The controller is also configured to align 3402 a second edge of the X-ray beam, which is opposite to the first edge of the X-ray beam, with a second edge of the collector 110, which is opposite to the first edge of the collector 110, while the X-ray beam emitter 100 and the collector are positioned with the second offset position 2310.

In some embodiments, the X-ray beam emitter 100 is moveable along a linear rail attached to the second end of the C-arm, as illustrated in FIG. 22. The controller is further configured to move the X-ray beam emitter 100 along the linear rail between the first offset position 2300 and second offset position 2310 relative to the collector 110. The X-ray beam emitter 100 can include a collimator that forms a window through which the X-ray beam is emitted toward the collector 110, where the collimator is configured to move a widow along the lateral axis. The controller is further configured to control movement of the window by the collimator to compensate for movement of the X-ray beam emitter 100 along the linear rail between the first offset position 2300 and second offset position 2310 to provide alignment of the X-ray beam with the collector 110.

The controller can be further configured to determine the first offset position 2300 and second offset position 2310 for the X-ray beam emitter 100 based on levels of scatter and transmission of the X-ray beam detected in images obtained from the collector 100 while the X-ray beam emitter is moved to each of the first offset position 2300 and second offset position 2310.

In some embodiments, the X-ray beam emitter 100 is moveable (angularly rotated) about an angular pivot attached to the second end of the C-arm, as illustrated in FIG. 23. The controller is further configured to angularly rotate the X-ray beam emitter 100 about the angular pivot between the first offset position 2300 and second offset position 2310 relative to the collector 110.

The controller can be further configured to determine the first offset position 2300 and second offset position 2310 for the X-ray beam emitter 100 based on levels of scatter of the X-ray beam detected in images obtained from the collector 110 while the X-ray beam emitter 100 is angularly rotated about the angular pivot between the first offset position 2300 and second offset position 2310.

In some embodiments, a collimator forms a window through which the X-ray beam is emitted toward the collector 110, and the collimator is configured to move a widow along the lateral axis. The controller is further configured to control movement of the window by the collimator to compensate for rotation of the X-ray beam emitter 100 about the angular pivot between the first offset position 2300 and second offset position 2310 to provide alignment of the X-ray beam with the collector 110.

Note that on the pivoting emitter setup, the emitter is closer to the collector at the traditional, centered position than at the first offset position 2300 and second offset position 2310. The magnitude of this difference depends on the length of the pivot arm. As long as the distance from the emitter to collector at the first offset position 2300 and second offset position 2310 are the same, the shapes of the volumes obtained from scans should be exactly inverse and when combined should form uniform double-length scans.

In some example embodiments, the C-arm spins the collector 110 and the X-ray beam emitter 100 at 30 degrees per second. One projection is used to produce an image per degree. An X-ray pulse of 10 ms is used to produce an image. Then back projection computing is used to weight the areas that overlap to combine the two sets of images.

Figure 24:
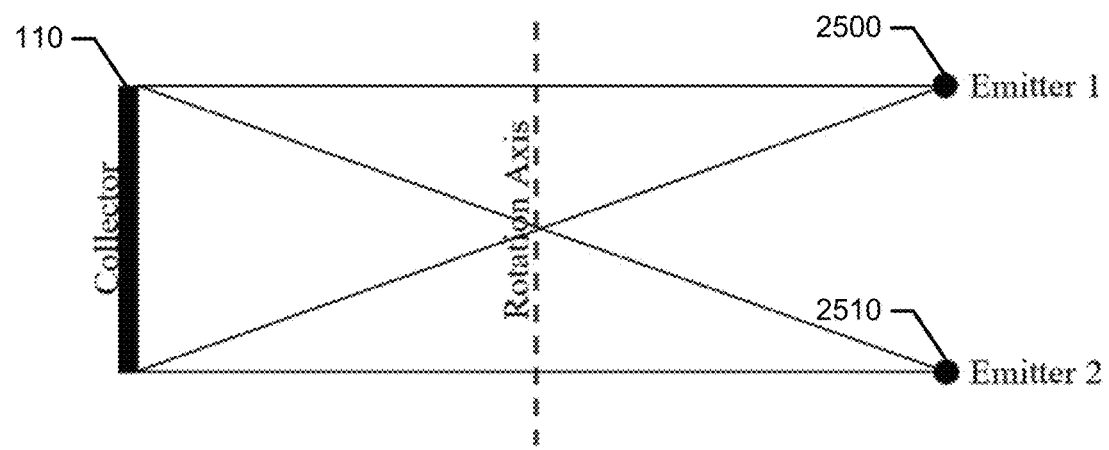
FIG. 24 illustrates the medical imaging system utilizing two fixed emitters with a single collector, in accordance with some embodiments of the present disclosure.

In some embodiments, the medical imaging system utilizes two fixed emitters with a single collector, as illustrated in FIG. 24. The medical imaging system includes a movable station having a C-arm, a collector 110, two X-ray beam emitters 2500 and 2510, and a controller. The C-arm has a first end and a second end that are movable along an arc relative to the movable station. The collector 110 is attached to the first end of the C-arm. The first X-ray beam emitter 2500 and a second X-ray beam emitter 2510 both face the collector 110 to emit X-ray beams in a direction of the collector 110 and both attached to the second end of the C-arm. The collector 110 and the first and second X-ray beam emitters 2500 and 2510 are spaced apart relative to each other along a lateral axis orthogonal to the arc. The controller is configured to obtain at least one set of images by rotating the collector and the first and second X-ray beam emitters along the arc about a scanned volume, and to combine the at least one set of images to generate a three-dimensional image of the scanned volume.

In some of these embodiments, the X-ray beams emitted by the first and second X-ray beam emitters 2500 and 2510 are aligned with the collector 110 while the controller obtains the at least one set of images.

In some embodiments the image volume generated from X-ray images using both X-ray beam emitters 2500 and 2510 are captured separately. The C-arm is spun once with the first X-ray beam emitter 2500 activated while capturing a first set of images, and the C-arm is then spun again with the second X-ray beam emitter 2510 activated while capturing a second set of images. The two sets of images are then combined.

In these embodiments, the controller is further configured to activate the first X-ray beam emitter 2500 to emit X-rays while maintaining the second X-ray beam emitter 2510 deactivated and while obtaining a first set of images by rotating the collector 110 and the first and second X-ray beam emitters 2500 and 2510 along the arc about a scanned volume. The controller is also configured to activate the second X-ray beam emitter 2510 to emit X-rays while maintaining the first X-ray beam emitter 2500 deactivated and while obtaining a second set of images by rotating the collector 110 and the first and second X-ray beam emitters 2500 and 2510 along the arc about the scanned volume. The controller is also configured to combine the first and second set of images to generate the three-dimensional image of the scanned volume.

In some embodiments, the image volume generated from X-ray images using both X-ray beam emitters 2500 and 2510 are captured by alternating phasing between X-ray beam emitters 2500 and 2510. The controller rapidly switches between the first X-ray beam emitter 2500 and the second X-ray beam emitter 2510 during one spin of the C-arm while generating two sets of images (one set from the first X-ray beam emitter 2500 and the other set from the second X-ray beam emitter 2510). The two sets of images are then combined.

In these dual emitter embodiments, the controller can be further configured to repetitively alternate between activation of the first X-ray beam emitter 2500 to emit X-rays while maintaining the second X-ray beam emitter 2510 deactivated and while obtaining an image for a first set of images and activation of the second X-ray beam emitter 2510 to emit X-rays while maintaining the first X-ray beam emitter 2500 deactivated and while obtaining an image for a second set of images, while rotating the collector 110 and the first and second X-ray beam emitters 2500 and 2510 along the arc about the scanned volume. The controller is also configured to combine the first and second set of images to generate the three-dimensional image of the scanned volume.

In some embodiments, the controller is further configured to repetitively alternate between an activation of the first X-ray beam emitter 2500 the activation of the second X-ray beam emitter 2510 at no more than one degree increments along the arc while rotating the collector and the first and second X-ray beam emitters 2500 and 2510 about the scanned volume.

The controller can be further configured to repetitively alternate between the activation of the first X-ray beam emitter 2500 the activation of the second X-ray beam emitter 2510 at no more than half degree increments along the arc while rotating the collector and the first and second X-ray beam emitters 2500 and 2510 about the scanned volume.

In some other dual emitter embodiments, the image volume generated from X-ray images captured using both X-ray beam emitters 2500 and 2510 are captured by simultaneously activating both X-ray beam emitters 2500 and 2510. The X-ray data is collected on the same collector 110 from both X-ray beam emitters 2500 and 2510 in one spin. Then the back-projections from these combined images are computed.

In these embodiments, the controller is further configured to simultaneously activate the first and second X-ray beam emitters to emit X-rays while obtaining a set of images while rotating the collector and the first and second X-ray beam emitters along the arc about the scanned volume. The controller is further configured to combine the set of images to generate the three-dimensional image of the scanned volume.

Figure 25:
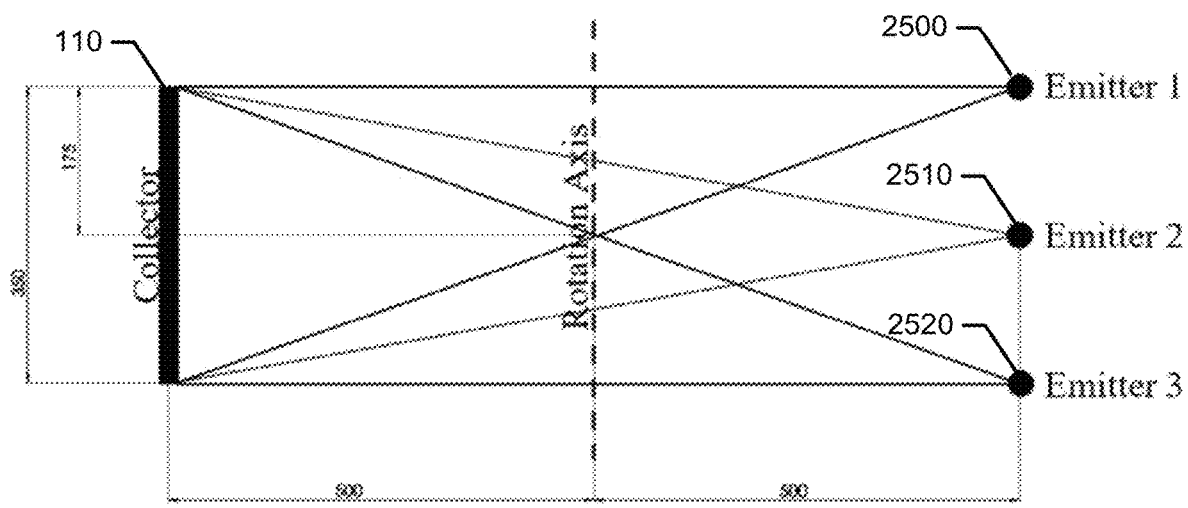
FIG. 25 illustrates a medical imaging system utilizing three fixed X-ray beam emitters with a single collector, in accordance with some embodiments of the present disclosure.

FIG. 25 illustrates a medical imaging system utilizing three fixed X-ray beam emitters 2600, 2610, and 2620 with a single collector 110. In some of these embodiments, traditional centered imaging uses the second X-ray beam emitter 2610 while the first and third X-ray beam emitters 2600 and 2620 remain deactivated.

In some embodiments, the medical imaging system collects a "double long" image using the first and third X-ray beam emitters 2600 and 2620, phased, sequentially, or simultaneously activated with the second X-ray beam emitters 2610 always deactivated.

In some embodiments, the medical imaging system collects a "high resolution" image using the first, second, and third X-ray beam emitters 2600, 2610, and 2620, phased, sequentially, or simultaneously activated. This creates an image with the region in the center being penetrated twice as much as other scans.

Figure 26:
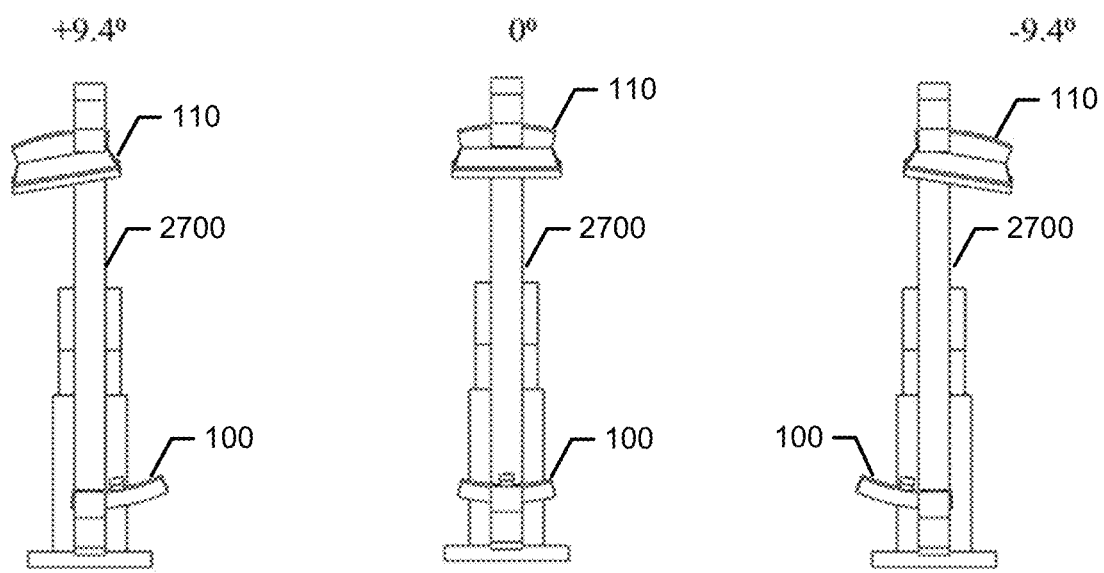
FIG. 26 illustrates three views of the collector and X-ray beam emitter rotated +9.4 degrees, 0 degrees, and −9.4 degrees.

In some embodiments, the medical imaging system has an additional axes and motors to produce an additional rotation distal to the other rotations, holding this offset angle during the spin. FIG. 26, FIG. 27, and FIG. 28 illustrate a medical imaging system having a C-arm 2700 with a controller configured to rotate the collector 110 and X-ray beam emitter 100 distal to the rotation of the C-arm 2700. FIG. 26 illustrates three views of the collector 110 and X-ray beam emitter 100 rotated +9.4 degrees, 0 degrees, and −9.4 degrees. FIGS. 27a-d illustrate four views of the C-arm rotating the collector 110 and X-ray beam emitter 100 along an arc while the collector 110 and the X-ray beam emitter are rotated +9.4 degrees distal to the other rotations during the spin. FIGS. 28a-d illustrate four views of the C-arm rotating the collector 110 and X-ray beam emitter 100 along an arc while the collector 110 and the X-ray beam emitter are rotated −9.4 degrees distal to the other rotations during the spin.

In some of these embodiments, the controller is further configured to angularly rotate the collector 110 and the X-ray beam emitter 100 toward each other in a first angular direction when the X-ray beam emitter 100 and the collector 110 are positioned with the first offset position 2300, and to angularly rotate the collector 110 and the X-ray beam emitter 100 toward each other in a second angular direction opposite to the first angular direction when the X-ray beam emitter 100 and the collector 110 are positioned with the second offset position 2310.

In some embodiments, FIGS. 29 and 30 illustrate a medical imaging system configured to include a movable collector 3000 and fixed X-ray beam emitter 3100. The collector 3000 has a linear bearing and motor, allowing it to move the collector 3000 to two different positions, in contrast to the embodiment of FIG. 22 which moved the X-ray beam emitter 3100 to two different positions and contrasted to the embodiment of FIG. 24 using multiple X-ray beam emitters. Moving the collector 3000 may involve moving the entire apparatus in a compensatory way (total movement=width of the collector plate) so that the collector 3000 via the apparatus movement remains in a fixed position relative to the patient. Additionally, collimators can be operated to move to different positions to allow the desired x-rays to reach the collector 3000 in its new position and block unused beams. FIG. 29 illustrates the collector 3000 in a first offset position. FIG. 30 illustrates the collector 3000 in a second offset position.

In some embodiments, the collector 3000 is moveable along a linear rail attached to the first end of the C-arm. The controller is further configured to move the collector 3000 along the linear rail between the first and second offset positions relative to the X-ray beam emitter 3010.

In some of the collector movement embodiments, the X-ray beam emitter 3010 comprises a collimator that forms a window through which the X-ray beam is emitted toward the collector 3000, wherein the collimator is configured to move a widow along the lateral axis. The controller is further configured to control movement of the window by the collimator to compensate for movement of the collector 3000 along the linear rail between the first and second offset positions to provide alignment of the X-ray beam with the collector 3000.

Figure 31:
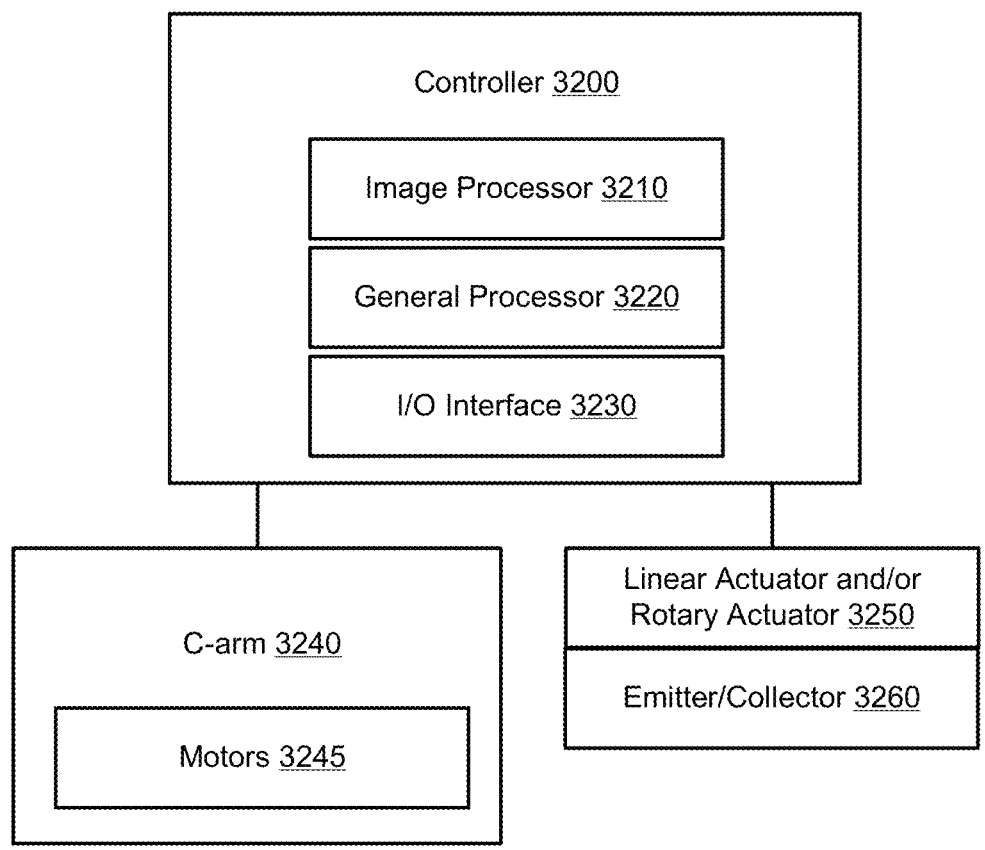
FIG. 31 illustrates a block diagram of components of a medical imaging system configured in accordance with some embodiments of the present disclosure.

FIG. 31 illustrates a block diagram of components of a medical imaging system configured in accordance with some embodiments of the present disclosure. The medical imaging system includes a controller 3200, a C-arm 3240, a linear actuator and/or rotary actuator 3250 connected to an X-ray beam emitter or collector 3260. The controller 3200 includes an image processor 3210, a general processor 3220, and an I/O interface 3230. The image processor 3210 performs mage processing to combine sets of images to generate a three-dimensional image of the scanned volume. The general processor 3220 is used to perform various embodiments of the present disclosure. The I/O interface 3230 communicatively couples the controller 3200 to other components of the medical imaging system. The C-arm 3240 includes motors 3245 used to move the collector and emitter along an arc, e.g., three hundred and sixty degrees, during image acquisition. Motors 3245 are controlled by C-arm the controller 3200. The controller 3200 can also control movement of the linear actuator and/or rotary actuator 3250.

Further Definitions and Embodiments

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented in entirely hardware without software or may be a combination of hardware and software executed by a computer controller.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A medical imaging system comprising:
a movable station including a C-arm having a first end and a second end that are movable along an arc relative to the movable station;
a collector attached to the first end of the C-arm;
an X-ray beam emitter facing the collector to emit an X-ray beam in a direction of the collector and attached to the second end of the C-arm; and
a controller configured to
move one of the X-ray beam emitter and the collector to a first offset position relative to each other along a lateral axis orthogonal to the arc,
obtain a first set of images by rotating the collector and the X-ray beam emitter along the arc about a scanned volume while the X-ray beam emitter and the collector are positioned with the first offset position,
move the one of the X-ray beam emitter and the collector to a second offset position relative to each other along the lateral axis orthogonal to the arc,
obtain a second set of images by rotating the collector and the X-ray beam emitter along the arc about the scanned volume while the X-ray beam emitter and the collector are positioned with the second offset position, and
combine the first and second set of images to generate a three-dimensional image of the scanned volume,
wherein the X-ray beam emitter is moveable along a linear rail attached to the second end of the C-arm; and
the controller is further configured to move the X-ray beam emitter along the linear rail between the first and second offset positions relative to the collector.

2. The medical imaging system of claim 1, wherein the controller is further configured to:
align a first edge of the X-ray beam with a first edge of the collector while the X-ray beam emitter and the collector are positioned with the first offset position; and
align a second edge of the X-ray beam, which is opposite to the first edge of the X-ray beam, with a second edge of the collector, which is opposite to the first edge of the collector, while the X-ray beam emitter and the collector are positioned with the second offset position.

3. The medical imaging system of claim 1, wherein:
the X-ray beam emitter comprises a collimator that forms a window through which the X-ray beam is emitted toward the collector, wherein the collimator is configured to move a widow along the lateral axis; and
the controller is further configured to control movement of the window by the collimator to compensate for movement of the X-ray beam emitter along the linear rail between the first and second offset positions to provide alignment of the X-ray beam with the collector.

4. The medical imaging system of claim 1, wherein:
the controller is further configured to determine the first and second offset positions for the X-ray beam emitter based on levels of scatter of the X-ray beam detected in images obtained from the collector while the X-ray beam emitter is moved to each of the first and second offset positions.

5. The medical imaging system of claim 1, wherein:
the controller is further configured to angularly rotate the collector and the X-ray beam emitter toward each other in a first angular direction when the X-ray beam emitter and the collector are positioned with the first offset position, and to angularly rotate the collector and the X-ray beam emitter toward each other in a second angular direction opposite to the first angular direction when the X-ray beam emitter and the collector are positioned with the second offset position.

6. The medical imaging system of claim 1, wherein:
the X-ray beam emitter is moveable about an angular pivot attached to the second end of the C-arm; and
the controller is further configured to angularly rotate the X-ray beam emitter about the angular pivot between the first and second offset positions relative to the collector.

7. The medical imaging system of claim 1, wherein:
the controller is further configured to determine the first and second offset positions for the X-ray beam emitter based on levels of scatter of the X-ray beam detected in images obtained from the collector while the X-ray beam emitter is angularly rotated about the angular pivot between the first and second offset positions.

8. The medical imaging system of claim 1, the X-ray beam emitter comprising:
a collimator that forms a window through which the X-ray beam is emitted toward the collector, wherein the collimator is configured to move a widow along the lateral axis; and
the controller is further configured to control movement of the window by the collimator to compensate for rotation of the X-ray beam emitter about the angular pivot between the first and second offset positions to provide alignment of the X-ray beam with the collector.

9. A medical imaging system comprising:
a movable station including a C-arm having a first end and a second end that are movable along an arc relative to the movable station;
a collector attached to the first end of the C-arm;
an X-ray beam emitter facing the collector to emit an X-ray beam in a direction of the collector and attached to the second end of the C-arm; and
a controller configured to
move one of the X-ray beam emitter and the collector to a first offset position relative to each other along a lateral axis orthogonal to the arc,
obtain a first set of images by rotating the collector and the X-ray beam emitter along the arc about a scanned volume while the X-ray beam emitter and the collector are positioned with the first offset position,
move the one of the X-ray beam emitter and the collector to a second offset position relative to each other along the lateral axis orthogonal to the arc,
obtain a second set of images by rotating the collector and the X-ray beam emitter along the arc about the scanned volume while the X-ray beam emitter and the collector are positioned with the second offset position, and
combine the first and second set of images to generate a three-dimensional image of the scanned volume,
wherein the collector is moveable along a linear rail attached to the first end of the C-arm; and
the controller is further configured to move the collector along the linear rail between the first and second offset positions relative to the X-ray beam emitter.

10. The medical imaging system of claim 9, wherein:
the X-ray beam emitter comprises a collimator that forms a window through which the X-ray beam is emitted toward the collector, wherein the collimator is configured to move a widow along the lateral axis; and
the controller is further configured to control movement of the window by the collimator to compensate for movement of the collector along the linear rail between the first and second offset positions to provide alignment of the X-ray beam with the collector.

11. A computer program product comprising a non-transitory computer readable medium storing program code executable by at least one processor of a controller of a medical imaging system for X-ray imaging to:
- move one of an X-ray beam emitter and a collector to a first offset position relative to each other along a lateral axis orthogonal to an arc,
- obtain a first set of images by rotating the collector and a X-ray beam emitter along the arc about a scanned volume while the X-ray beam emitter and the collector are positioned with the first offset position,
- move the one of the X-ray beam emitter and the collector to a second offset position relative to each other along the lateral axis orthogonal to the arc,
- obtain a second set of images by rotating the collector and the X-ray beam emitter along the arc about the scanned volume while the X-ray beam emitter and the collector are positioned with the second offset position, and
- combine the first and second set of images to generate a three-dimensional image of the scanned volume,
- move the X-ray beam emitter along a linear rail between the first and second offset positions relative to the collector and/or to angularly rotate the collector and the X-ray beam emitter toward each other in a first angular direction when the X-ray beam emitter and the collector are positioned with the first offset position and to angularly rotate the collector and the X-ray beam emitter toward each other in a second angular direction opposite to the first angular direction when the X-ray beam emitter and the collector are positioned with the second offset position.

* * * * *